(12) United States Patent
Leue et al.

(10) Patent No.: US 6,486,320 B2
(45) Date of Patent: Nov. 26, 2002

(54) PREPARATION OF CAMPTOTHECIN AND OF ITS DERIVATIVES

(75) Inventors: Stefanie Leue, Chantilly (FR); Stéphanie Garçon, Grenoble (FR); Andrew-Elliot Greene, Uriage (FR); Yves Génisson, Toulouse (FR); Patrick Léon, Tassin la Demi Lune (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/951,505

(22) Filed: Sep. 14, 2001

(65) Prior Publication Data

US 2002/0045756 A1 Apr. 18, 2002

Related U.S. Application Data

(60) Provisional application No. 60/240,080, filed on Oct. 16, 2000.

(30) Foreign Application Priority Data

Sep. 15, 2000 (FR) .............................................. 00 11769

(51) Int. Cl.⁷ .................... C07D 491/14; C07D 405/12; C07D 471/04
(52) U.S. Cl. .............................. 546/48; 84/157; 84/175
(58) Field of Search .......................... 546/48, 157, 175, 546/84

(56) References Cited

U.S. PATENT DOCUMENTS

| | | | |
|---|---|---|---|
| 4,473,692 A | 9/1984 | Miyasaka et al. | 546/48 |
| 4,545,880 A | 10/1985 | Miyasaka et al. | 204/158 R |
| 4,604,463 A | 8/1986 | Miyasaka et al. | 546/48 |
| 5,525,731 A | * 6/1996 | Danishefsky et al. | 546/48 |

FOREIGN PATENT DOCUMENTS

| | | |
|---|---|---|
| EP | 0 056 692 B1 | 7/1982 |
| EP | 0 074 256 B1 | 3/1983 |
| EP | 0 088 642 A2 | 9/1983 |
| EP | 0 296 612 B1 | 12/1988 |
| EP | 0 321 122 B1 | 6/1989 |
| EP | 0 325 247 B1 | 7/1989 |
| EP | 0 540 099 B1 | 5/1993 |
| EP | 0 737 686 B1 | 10/1996 |
| JP | 57-116015 | 7/1982 |
| JP | 57-116074 | 7/1982 |
| JP | 59-5188 | 1/1984 |
| JP | 59-51289 | 3/1984 |
| JP | 60-19790 | 1/1985 |
| JP | 1-246287 | 10/1989 |
| JP | 1-249777 | 10/1989 |
| WO | WO 90/03169 | 4/1990 |
| WO | WO 96/37496 | 11/1996 |
| WO | WO 96/38146 | 12/1996 |
| WO | WO 96/38449 | 12/1996 |
| WO | WO 97/00876 | 1/1997 |

OTHER PUBLICATIONS

Abstract: Japio No. 00965715 for JP 57–116015.
Abstract: Japio No. 00965774 for JP 57–116074.
Abstract: Japio No. 01293588 for JP 59–5188.
Abstract: Japio No. 01541290 for JP 60–19790.
Abstract: Japio No. 02948687 for JP 1–246287.
Abstract: Japio No. 02952177 for JP 1–249777.
Abstract: Derwent No. 01984–110813/198418 for JP 59–051289.
M. A. Ciufolini and F. Roschangar, "Practical Total Synthesis of (+)–Camptothecin: The Full Story," *Tetrahedron*, 53(32):11049–11060 (1997).
S. Sawada, S. Okajima, R. Aiyama, K. Nokata, T. Furuta, T. Yokokura, E. Sugino, K. Yamaguchi, and T. Miyasaka, "Synthesis and Antitumor Activity of 20(S)–Camptothecin Derivatives: Carbamate–Linked, Water–Soluble Derivatives of 7–Ethyl–10–Hydroxycamptohecin," *Chem. Pharm. Bull.*, 39(6): 1446–1454 (1991).
S. Sawada, K. Nokata, T. Furuta, T. Yokokura, and T. Miyasaka, "Chemical Modification of an Antitumor Alkaloid Camptothecin: Synthesis and Antitumor Activity of 7–C–Substituted Camptothecins," *Chem. Pharm. Bull.*, 39(10):2574–2580 (1991).
S. Sawada, S. Matsuoka, K. Nokata, H. Nagata, T. Furuta, T. Yokokura, and T. Miyasaka, "Synthesis and Antitumor Activity of 20(S)–Camptothecin Derivatives: A–Ring Modified and 7,10–Disubstituted Camptothecins," *Chem. Pharm. Bull.*, 39(12): 3183–3188 (1991).
S. Sawada and T. Yokokura, "The Camptothecins From Discovery to the Patient: Synthesis of CPT–11 (Irinotecan Hydrochloride Trihydrate)," *Annals of the New York Academy of Sciences*, 803:13–28 (1996).

* cited by examiner

Primary Examiner—Bernard Dentz
(74) Attorney, Agent, or Firm—Finnegan, Henderson, Farabow, Garrett & Dunner LLP

(57) ABSTRACT

The present invention relates to a novel process for preparation of camptothecin and of its derivatives by convergent synthesis starting from a 3-(aminomethyl)quinoline derivative and 5-hydroxy-5-ethyl-6-oxo-5,6-dihydropyrancarboxylic acid and to the intermediates obtained.

45 Claims, No Drawings

PREPARATION OF CAMPTOTHECIN AND OF ITS DERIVATIVES

This application claims priority from Provisional Application Ser. No. 60/240,080 filed Oct. 16, 2000.

The present invention relates to the preparation of camptothecin and of its derivatives. It relates more particularly to the preparation of camptothecin, of topotecan and of irinotecan.

Camptothecin derivatives of general formula:

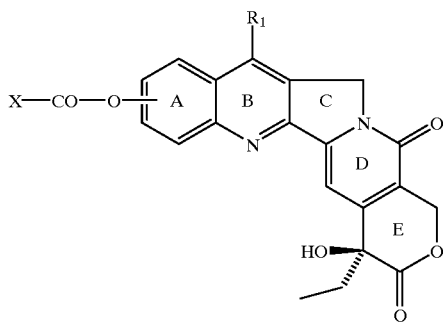

in which in particular $R_1$ is hydrogen, halogen or alkyl and X is a chlorine atom or $NR_2R_3$ for which $R_2$ and $R_3$, which are identical or different, can represent a hydrogen atom, an optionally substituted alkyl radical, an optionally substituted carbocyclyl, an optionally substituted heterocycle or alkyl radicals (optionally substituted) which form, with the nitrogen atom to which they are attached, a heterocycle optionally comprising another heteroatom chosen from O, S and/or $NR_4$, $R_4$ being a hydrogen atom or an alkyl radical, and in which the X—CO—O— group is situated at the 9-, 10- or 11-position of the A ring are known according to European Patent EP 137 145, cited here by way of reference. These camptothecin derivatives are anticancer agents which are topoisomerase I inhibitors, among which irinotecan, for which X—CO—O— is [4-(1-piperidino)-1-piperidino] carbonyloxy, is an active principle which is particularly effective with respect to solid tumours and in particular colorectal cancer.

Other camptothecin derivatives which are mentioned as anticancer agents, in particular derivatives with a structure analogous to the structure given above, in which structure X—CO—O— is replaced by an —X'R' radical for which X' is O or S and R' is a hydrogen atom or an alkyl or acyl radical, are also known according to Patent Application EP 74 256, cited here by way of reference.

Other camptothecin derivatives have also been disclosed, for example in the patents or patent applications, cited here by way of reference, EP 56 692, EP 88 642, EP 296 612, EP 321 122, EP 325 247, EP 540 099, EP 737 686, WO 9003169, WO 9637496, WO 9638146, WO 9638449, WO 9700876, U.S. Pat. No. 7,104,894, JP 57 116015, JP 57 116074, JP 59 005188, JP 60 019790, JP 01 249777, JP 01246287 or JP 91 012070, or in Canc. Res., 38 (1997) Abst. 1526 or 95 (San Diego, April 12–16), Canc. Res., 55(3), 603–609 (1995) or AFMC Int. Med. Chem. Symp. (1997) Abst. PB-55 (Seoul, July 27-August 1).

Irinotecan (CPT-11) and its derivatives are usually prepared from natural camptothecin (U.S. Pat. No. 4,604,463; S. Sawada et al., Chem. Pharm. Bull., 39, 2574–80 (1991), Chem. Pharm. Bull., 39, 1446–54 (1991), Chem. Pharm. Bull., 39, 3183–88 (1991) and Ann. N.Y. Acad. Sci., 803, 13–28 (1996). The stages comprise the introduction of a hydroxyl functional group at the 9-position, an alkylation at the 11-position and the introduction of a radical at the 9-position.

International Patent Application WO 96/31513 has disclosed the preparation of mappicine and camptothecin derivatives by total synthesis by firstly preparing the C-D or C-D-E ring sequence.

Tetrahedron, 53(32), 11049–60 (1997), also describes total syntheses of camptothecin derivatives in which the A-B and D-E rings are prepared beforehand or, according to another aspect, the C-D-E or A-B-C sequences.

It has now been found, and it this which forms the subject matter of the present invention, that camptothecin or camptothecin derivatives of following formula (I):

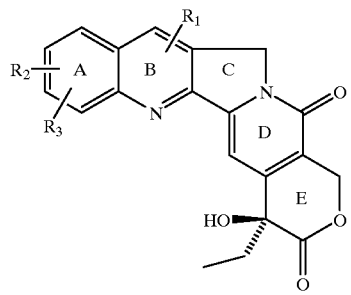

(I)

in which $R_1$, $R_2$ and $R_3$ each represent an identical or different group chosen from:
hydrogen,
a hydroxyl group,
a halogen atom chosen from fluorine, chlorine, bromine or iodine,
linear or branched alkoxy groups comprising 1 to 4 carbon atoms,
linear or branched alkylthio groups comprising 1 to 4 carbon atoms,
$(C_1-C_4)$alkylamino groups optionally substituted by one or more $C_1-C_4$ alkyl groups,
aralkyl groups optionally substituted by a $C_1-C_4$ alkyl group, said aryl groups also optionally being heterocycles comprising 1 to 3 heteroatoms chosen from oxygen, sulfur and nitrogen,
arylcarbonyloxy groups, said aryl groups also optionally being mono- or polycyclic heterocycles comprising 1 to 3 heteroatoms chosen from oxygen, sulfur and nitrogen, can be obtained by a convergent synthesis starting from a 3-(aminomethyl)quinoline derivative and 5-hydroxy-5-ethyl-6-oxo-5,6-dihydropyrancarboxylic acid with particularly advantageous results.

The preferred and commercial compounds synthesized by the process of the invention are:
camptothecin, for which $R_1$, $R_2$ and $R_3$ represent hydrogen,
topotecan or Hycamtin®, for which $R_1$ is hydrogen, $R_2$ represents a dimethylamino-methyl group and $R_3$ represents a hydroxyl group,
irinotecan or Campto®, for which $R_1$ represents an ethyl group, $R_2$ represents a piperidinopiperidinocarbonyloxy group and $R_3$ represents hydrogen.

The process according to the invention consists in condensing a 3-(aminomethyl)quinoline derivative and 5-hydroxy-5-ethyl-6-oxo-5,6-dihydro-pyrancarboxylic acid, followed by an ethynylation stage, optionally by a hydrolysis stage, by a double cyclization stage, by a dehydrogenation and by a deprotection/dealkoxycarbonylation stage.

According to the invention, 5-hydroxy-5-ethyl-6-oxo-5,6-dihydropyrancarboxylic acid with the structure:

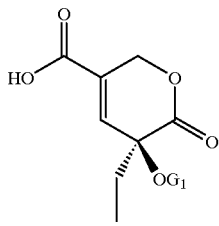

(II)

in which $G_1$, represents hydrogen or a protective group for the hydroxyl functional group chosen in particular from the benzyl, para-methoxybenzyl, methoxymethyl, tert-butyl and trialkylsilyl groups, at least one alkyl group in the trialkylsilyl having more than two carbon atoms, is condensed with a 3-(aminomethyl)quinoline derivative of general formula:

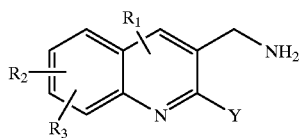

(III)

in which $R_1$, $R_2$ and $R_3$ have the same meaning as in the formula (I) or represent protected radicals or radicals which can be easily converted to $R_1$, $R_2$ and $R_3$ radicals mentioned above and Y represents a leaving group chosen in particular from halogen atoms or an $OSO_2R$ radical where R represents an alkyl, tolyl, naphthyl or trifluoromethyl group, in order to obtain the quinoline derivative of general formula:

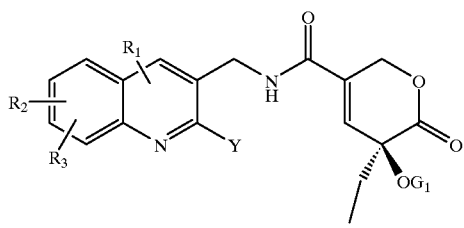

(IV)

in which $G_1$, $R_1$, $R_2$, $R_3$ and Y are defined as above.

The benzyl group is preferred among the $G_1$ groups. Preference is given, among the Y groups, to halogens chosen from bromine or iodine and, among the $OSO_2R$ groups, to trifluoromethylsulfonate.

The reaction is generally carried out according to the usual methods for condensing acids with amines, in particular by reaction with the acid or a reactive or activated derivative of the acid.

When the condensation of a reactive derivative of the acid of general formula (II) is carried out, the reaction is advantageously carried out by means of the acid chloride, of the anhydride, of a mixed anhydride or of a reactive ester, or of an ammonium or pyridinium acyl intermediate.

It is preferable, among the reaction conditions, to use a temperature of between −40 and +40° C. It is preferable, among the inert solvents which can be used, to use an organic solvent such as in particular a chlorinated solvent (dichloromethane, dichloroethane or chloroform, for example). The reaction can optionally be carried out in the presence of an acid acceptor, such as a nitrogenous organic base, such as, for example, pyridine, dimethylaminopyridine, N-methylmorpholine or a trialkylamine (in particular triethylamine or diisopropylethylamine). It is also preferable to carry out the reaction in the presence of a coupling agent, such as a carbodiimide [for example dicyclohexylcarbodiimide or 1-(3-(dimethylamino)propyl)-3-ethylcarbodiimide], N,N'-carbonyldiimidazole or 2-ethoxy-1-ethoxycarbonyl-1,2-dihydroquinoline. The reaction is preferably carried out under argon or nitrogen.

It is understood that the amino, alkylamino or carboxyl radicals present in $R_1$, $R_2$ and $R_3$, like the hydroxyl functional group carried by the pyran ring, are preferably protected beforehand. Protection is carried out in particular according to the methods described by T. W. Greene and P. G. M. Wuts, Protective Groups in Organic Synthesis (3$^{rd}$ ed.), A. Wiley-Interscience Publication (1999).

Subsequently, the quinoline derivative of general formula (IV) and trialkyl (optionally substituted $C_1$–$C_4$) orthopropiolate or alkyl (optionally substituted $C_1$–$C_4$) propiolate are reacted in the presence of a palladium complex [such as, for example, tris(dibenzylideneacetone)dipalladium, bis(benzonitrile)palladium chloride or dichlorobis(triphenylphosphine)palladium] and of copper iodide and of a base, such as a tertiary amine (trialkylamine) or of an alkaline carbonate, to give the quinoline derivative of general formula:

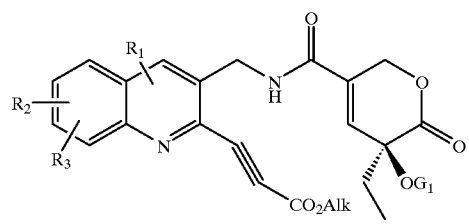

(V)

in which $R_1$, $R_2$, $R_3$ and $G_1$ are defined as above and Alk represents a $C_1$–$C_4$ alkyl group optionally substituted by an aryl or heteroaryl group.

When the condensation is carried out in the presence of trialkyl (optionally substituted $C_1$–$C_4$) orthopropiolate, a hydrolysis stage is carried out after the condensation stage.

The condensation reaction is preferably carried out in an inert organic solvent, such as an ether (dioxane, for example), or in an amide, such as acetamide or dimethylformamide, at a temperature of between 20 and 110° C. This temperature is preferably between 20 and 80° C. and the reaction is carried out under argon or nitrogen.

The quinoline derivative of general formula (V) is subsequently cyclized by addition of a base, preferably in the presence of DBU (1,8-diazabicyclo[5.40]undec-7-ene) or of DBN (1,5-diazabicyclo[5.4.0]non-5-ene or of DABCO (1,4-diazabicyclo[2.2.2]octane, to give the tetracyclic derivative of general formula (VI):

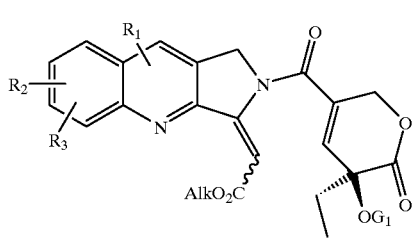

(VI)

in which Alk, $R_1$, $R_2$, $R_3$ and $G_1$ are defined as above.

As regards the reaction conditions, the reaction is preferably carried out in an anhydrous medium, in an inert organic solvent, such as an aromatic solvent (for example toluene), at a temperature of between −30 and +30° C. The reaction is preferably carried out under argon or under nitrogen.

This derivative is subsequently subjected to a cyclization to give the ester of protected camptothecin and/or of its derivatives of general formula:

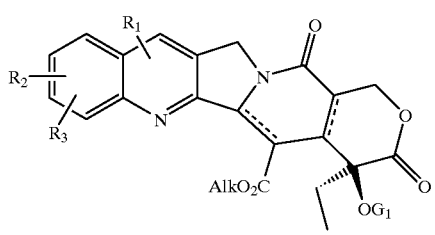

(VII)

in which $R_1$, $R_2$, $R_3$, Alk and $G_1$ are defined as above.

The cyclization is preferably carried out by irradiation. The irradiation is carried out alone, in the presence of an oxidizing agent, such as iodine, or with a reducing agent, such as a borohydride.

The irradiation is generally carried out in an organic solvent chosen in particular from halogenated aliphatic solvents (for example, dichloromethane or chloroform), in the first two cases mentioned above, or an alcohol (for example methanol), for the final case mentioned above, at a temperature preferably of between −30° C. and 50° C.

The derivative of formula (VII) above which does not have a double bond either on the lactone or on the piperidone and where Alk is a methyl group substituted by an aryl or heteroaryl group is subsequently hydrogenated in the presence of a palladium catalyst to give the acid, which is converted to camptothecin and/or its derivatives by the action of palladium and cymene at high temperature, optionally followed by a deprotection of the hydroxyl group on the lactone.

The derivative of formula (VII) above which has one double bond or optionally none on the piperidone can be treated with DDQ (dichlorodicyanobenzoquinone) to give the compound of formula (VII) with the two double bonds.

The derivative of general formula (VII) having two double bonds on the lactone and on the piperidone ring is finally deprotected and dealkoxycarbonylated by the action of hydrobromic acid at a temperature of between 50 and 140° C., to give camptothecin or its derivatives of general formula (I):

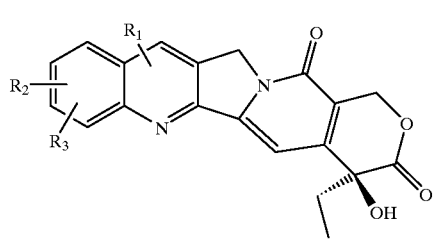

(I)

The 3-(aminomethyl)quinoline derivative of general formula (III) in which $R_1$, $R_2$, $R_3$ and Y are defined as above can be prepared by reduction of the corresponding 3-(azidomethyl)quinoline derivative of general formula:

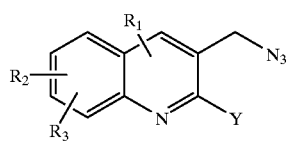

(VIII)

in which $R_1$, $R_2$, $R_3$ and Y are defined as above.

The reduction is carried out, for example, by catalytic hydrogenation in the presence of platinum oxide in an alcoholic medium (for example, ethanol or methanol) at a temperature of between 0 and 30° C.

The 3-(azidomethyl)quinoline derivative of general formula (VIII) is prepared from the 3-methyl-quinoline derivative of general formula:

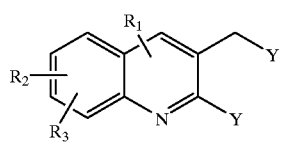

(IX)

in which $R_1$, $R_2$, $R_3$ and Y are defined as above, the Y groups being identical or different.

The reaction is generally carried out by reaction with sodium azide in an organic solvent, such as an amide (for example dimethylformamide), at a temperature in the region of 20° C. The reaction is preferably carried out under argon or under nitrogen.

5-Hydroxy-5-ethyl-6-oxo-5,6-dihydropyran-carboxylic acid of formula (II) is prepared from the $C_1$–$C_4$ alkyl ($Alk_1$) ester of 2-hydroxybutyric acid, the hydroxyl functional group of which is protected, by condensation with a compound of formula (X) in which $Alk_2$ represents a $C_1$–$C_4$ alkyl group

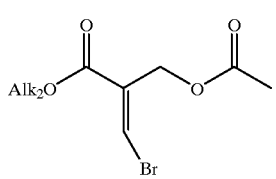

(X)

to give the compound of following formula (XI)

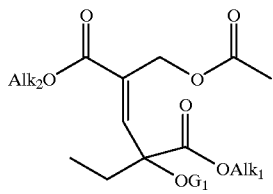

(XI)

in the presence of a strong base, such as an alkyllithium, LDA, alkaline hexamethyldisilazide (for example lithium hexamethyldisilazide) or alkaline tetramethylpiperidide (for example lithium tetramethylpiperidide), in an inert solvent (for example an ether, such as tetrahydrofuran).

The reaction is maintained in particular between −80 and −40° C.

The cyclization of the compound of formula (XI) is carried out in particular to the compound of following formula (XII):

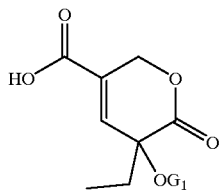

(XII)

in which $G_1$ represents a hydrogen atom or a protective group for the alcohol functional group, in the presence of a base, such as an alkaline hydroxide or an alkaline alkoxide (for example, lithium hydroxide or sodium ethoxide), in an inert solvent, such as an ether or an alcohol, at a temperature of in particular between 0 and 40° C. When the base used is an alkaline hydroxide, the saponification of the ester is carried out simultaneously; when the base used is an alkaline alkoxide, the saponification of the ester is carried out subsequently, in particular in the presence of an alkaline hydroxide. Finally, the compound is resolved according to methods known to a person skilled in the art.

The compound of formula (X) is prepared according to, for example, the protocol described by Ben Ayed, Amri and El Gaied in Tetrahedron, 1991, 47, p. 9621–9628.

The products obtained according to the process, camptothecin and its derivatives, can be purified according to the usual methods used by a person skilled in the art. For example by chromatography.

Camptothecin derivatives are usually administered by the injectable route, more particularly by the intravenous route, in the form of a sterile solution or of an emulsion. Camptothecin derivatives can also be administered by the oral route, in the form of solid or liquid compositions.

When the camptothecin derivative is administered by the intravenous route, these compositions can also comprise adjuvants, in particular wetting, isotonizing, emulsifying, dispersing and stabilizing agents. Irinotecan (CPT-11) is in particular administered in solution in a medium for intravenous injection, at doses of between 175 to 500 mg/m².

The products of formula III, IV, V, VI, VII, VIII, XI and XII are claimed individually as novel intermediates.

The following examples, given without implying limitation, illustrate the present invention.

EXAMPLES

2-Bromoquinolin-3-ylmethyl azide (IX)

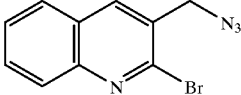

1.363 g (21 mmol) of $NaN_3$ are added, under an argon atmosphere, to a mixture of 803 mg (2.67 mmol) of dibromide and 11 ml of DMF. The mixture is stirred for 12 hours at room temperature and subsequently hydrolysed with a saturated aqueous NaCl solution.

The aqueous phase is extracted with $CH_2Cl_2$ and the combined organic phases are washed 3 times with water. After drying over $Na_2SO_4$ and evaporating under reduced pressure, chromatography on silica gel (eluent: pentane/10%–15% $Et_2O$) makes it possible to obtain 597 mg (2.27 mmol, 85%) of product (IX) in the form of an off-white solid.

IR ($CH_2Cl_2$): $v=2104$ ($N_3$) $cm^{-1}$.

$^1$H NMR (200 MHz, $CDCl_3$): $\delta=4.60$ (s, 2H, $CH_2$), 7.55 (ddd, 1H, aromat. H, $^3J=7.9$, 7.0 Hz, $^4J=1.4$ Hz), 7.68 (ddd, 1H, aromat. H, $^3J=8.2$, 7.0 Hz, $^4J=1.4$ Hz), 7.78 (dd, 1H, aromat. H, $^3J=7.9$ Hz, $^4J=1.4$ Hz), 7.99 (dd, 1H, aromat. H, $^3J=8.2$ Hz, $^4J=1.4$ Hz), 8.06 (s, 1H, aromat. H). $^{13}$C NMR (200 MHz, $CDCl_3$): $\delta=53.7$ ($CH_2$), 127.0 (C), 127.5 (CH), 127.6 (CH), 128.3 (CH), 129.4 (C), 130.7 (CH), 136.8 (CH), 142.2 (C), 147.7 (C).

MS (EI, high resolution): Calculated: 261.9854 Found: 261.9860

Melting point: 54–56° C.

Elemental analysis: Calculated: C 45.65%, H 2.68%, N 21.30% Found: C 45.75%, H 2.70%, N 20.96%

C-(2-Bromoquinolin-3-yl)methylamine (III)

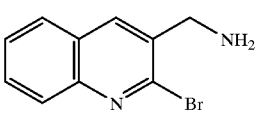

30 mg (0.13 mmol, 3%) of $PtO_2$ is added, under an argon atmosphere, to a solution of 1.015 g (3.86 mmol) of product (IX) in 110 ml of ethanol. The reaction medium is placed under a hydrogen atmosphere and stirring is maintained for 2 hours at room temperature. After filtering through celite and evaporating under reduced pressure, 863 mg (3.64 mmol, 99%) of a slightly yellow solid are obtained. The residue is used directly in the following reaction.

IR (KBr): $v=3338$ (NH), 1614 (C=C), 1586, 1556 $cm^{-1}$ $^1$H NMR (200 MHz, DMSO): $\delta=3.92$ (s, 2H, $CH_2$), 7.70 (m, 2H, aromat. H), 7.98 (m, 2H, aromat. H), 8.43 (s, 1H, aromat. H).

$^{13}$C NMR (200 MHz, DMSO): $\delta=44.9$ ($CH_2$), 127.3 (CH), 127.5 (CH), 127.8 (CH), 129.9 (CH), 135.9 (CH), 137.0 (C), 143.3 (C), 146.5 (C).

MS (EI, high resolution): Calculated: 235.9949 Found: 235.9954

Melting point: 131° C.

2-(Hydroxymethyl)acrylic acid ethyl ester (XIV)

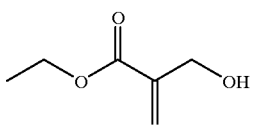

The product (XIV) is prepared according to the protocol of Villiéras and coworkers [J. Villiéras, M. Rambaud, *Synthesis*, 1982, 924] from 18.5 g (82.2 mmol) of triethyl phosphonoacetate, 30 ml of a 37% aqueous formaldehyde solution and 19.5 g of potassium carbonate dissolved in 20 ml of water. Purification by chromatography on silica gel (eluent: pentane/10–100% Et$_2$O) makes it possible to obtain 6.2 g (47.7 mmol, 58%) of the expected product. The spectroscopic data correspond to those described in the reference.

Ethyl ester of 2-(acetoxymethyl)acrylic acid (XV)

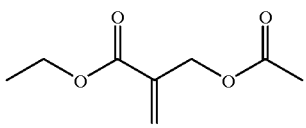

The product is prepared according to the protocol of Amri and coworkers [H. Amri, M. Rambaud and J. Villiéras, *J. Org. Chem.*, 1990, 384, 1–11] from 2.0 g (15.4 mmol) of product (XIV), 9.3 ml of diethyl ether, 5.83 ml (6.3 g, 62 mmol) of acid anhydride and one drop of concentrated sulfuric acid. Purification by chromatography on silica gel (eluent: pentane/10% Et$_2$O) makes it possible to obtain 2.4 g (12.8 mmol, 83%) of product.

IR (Film): ν=1750 (C=O), 1727 (C=O), 1647 (C=C), 1233 (Ac)cm$^{-1}$.

$^1$H NMR (200 MHz, CDCl$_3$): δ=1.24 (t, 3H, CH$_2$, CH$_3$, $^3$J=7.2 Hz), 2.04 (s, 3H, C=OCH$_3$), 4.18 (q, 2H, CH$_2$CH$_3$, $^3$J=7.2 Hz), 4.74 (s, 2H, CH$_2$C=C), 5.77 (m, 1H, C=CH), 6.29 (m, 1H, C=CH).

Ethyl ester of 2-acetoxymethyl-2,3-dibromopropionic acid (XVI)

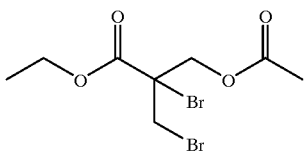

The above product is prepared according to the protocol of Amri and coworkers [T. Ben Ayed, H. Amri, M. M. El Gaied, *Tetrahedron*, 1991, 47, 9621–9628] from 1.0 g (5.8 mmol) of product (XV), 15 ml of tetrachloromethane and 0.31 ml (0.967 g, 6.04 mmol) of bromine. Purification by chromatography on silica gel (eluent: pentane/10% Et$_2$O) makes it possible to obtain 1.6 g (4.82 mmol, 83%) of the expected product. On using CH$_2$Cl$_2$ as solvent, a yield of 94% is achieved.

IR (Film): ν=2991, 2941, 2907, 2876, 1749 (C=O), 1620 (C=C), 1225 (Ac)cm$^{-1}$.

$^1$H NMR (200 MHz, CDCl$_3$): δ=1.32 (t, 3H, CH$_2$CH$_3$, $^3$J=7.2 Hz), 2.12 (s, 3H, C=OCH$_3$), 3.99 (ABq, 2H, CH$_2$Br, δ$_a$-δ$_b$=0.176, δ$_a$=4.08, δ$_b$=3.90, $^2$J$_{AB}$=10.28 Hz), 4.31 (q, 2H, CH$_2$CH$_3$, $^3$J=7.2 Hz), 4.65 (ABq, 2H, CH$_2$O—COCH$_3$[lacuna]=0.131, δ$_a$=4.53, δ$_b$=4.40, $^2$J$_{AB}$=12.7 Hz).

$^{13}$C NMR (200 MHz, CDCl$_3$): δ=14.8 (CH$_3$), 21.6 (CH$_3$), 34.0 (CH$_2$), 57.5 (C), 63.9 (CH$_2$), 65.7 (CH$_2$), 167.6 (C=O), 170.8 (C=O).

Ethyl ester of (E)-2-acetoxymethyl-3-bromoacrylic acid (XI)

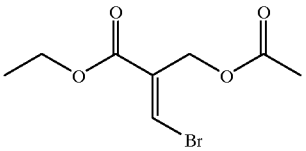

The product (XI) is prepared according to the protocol of Amri and coworkers [T. Ben Ayed, H. Amri, M. M. El Gaied, *Tetrahedron*, 1991, 47, 9621–9628] from 10.0 g (30 mmol) of product of formula (XVI) obtained in the preceding stage, 13.4 g (45 mmol) of tetrabutylammonium fluoride and 20 ml of HMPA. Purification by chromatography on silica gel (eluent: pentane/10% Et$_2$O) makes it possible to obtain 4.14 g (16.5 mmol, 55%) of the expected product.

IR (Film): ν=1747 (C=O), 1722 (C=O), 1616 (C=C), 1227 (Ac) cm$^{-1}$.

$^1$H NMR (200 MHz CDCl$_3$: δ=1.25 (t, 3H, CH$_2$CH$_3$, $^3$J=7.2 Hz), 2.00 (s, 3H, COCH$_3$), 4.19 (q, 2H, CH$_2$CH$_3$, $^3$J=7.2 Hz), 4.90 (s, 2H, CH$_2$C=C), 7.75 (s, 1H, C=CH).

2-Benzyloxybutyric acid

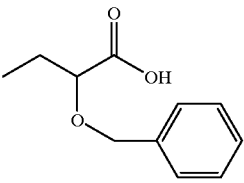

9 ml (9.72 g, 90 mmol) of benzyl alcohol and 10.02 g (60 mmol) of α-bromobutyric acid (191) are added to a mixture of 12 g (300 mmol) of NaH in 300 ml of THF. Stirring is maintained for 30 minutes at room temperature and the suspension is subsequently brought to 50° C. for 15 hours. The mixture is poured onto ice and extracted with Et$_2$O. The ethereal phase is washed with a mixture of water and a small amount of solid NaHCO$_3$. The combined aqueous phases are acidified with aqueous HCl (5%) and extracted with Et$_2$O. After drying over Na$_2$SO$_4$, the solvent is evaporated under reduced pressure. 12 g of crude product are obtained, which product is used without purification in the following reaction and which product still comprises a small amount of α-bromobutyric acid.

$^1$H NMR (200 MHz, CDCl$_3$): δ=1.0 (t, 3H, CHCH$_2$CH$_3$ $^3$J=7.54 Hz), 1.87 (m, 2H, CHCH$_2$CH$_3$), 3.95 (m, 1H, CHCH$_2$CH$_3$), 4.60 (ABq, 2H, CH$_2$Ph, $^2$J$_{AB}$=11.3 Hz, δ$_a$=4.71, δ$_b$=4.49, δ$_a$-δ$_b$=0.22), 7.34 (m, 5H, aromatic H).

Methyl ester of 2-benzooxybutyric acid

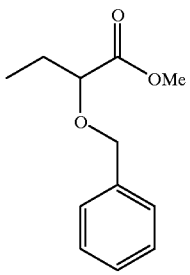

The crude 2-benzyloxybutyric acid (12 g) is dissolved in $Et_2O$, and diazomethane in ether is subsequently added dropwise until the yellow color persists. After adding acetic acid, the solution is washed with water, dried over $Na_2SO_4$ and evaporated under reduced pressure. Purification by chromatography on silica gel (eluent: pentane/10% $Et_2O$) makes it possible to isolate 5.9 g (28.5 mmol, 48% over two stages) of the expected product. The data of the spectra correspond to those described in the reference [K. Horita, T. Inoue, K. Tanaka and O. Yonemitsu, *Tetrahedron*, 1996, 52, 531–550].

The product can be synthesized according to the protocol of Satoh and coworkers [H. Iwamura, Y. Imahashi, K. Kushida, K. Aoki and S. Satoh, *Bull. Chem. Soc. Jpn.*, (1976), 49, 1690–1696].

Ethyl ester of 2-benzyloxybutyric acid

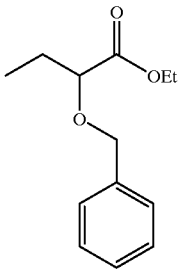

1ml of concentrated $H_2SO_4$ is added, under an argon atmosphere, to a solution of 12 g of crude 2-benzyloxybutyric acid in 50 ml of dry ethanol, followed by flame-dried molecular sieve. The mixture is brought to reflux and stirring is maintained for 18 hours. The suspension is subsequently filtered through a sintered glass filter, diluted with 100 ml of ethyl acetate and washed 3 times with a saturated aqueous NaCl solution. The organic phase is dried over $Na_2SO_4$, evaporated under reduced pressure and purified by chromatography on silica gel (eluent: pentane/10% $Et_2O$). 7.5 g (33.8 mmol, 56% over 2 stages) of product are obtained.

IR (Film): $\nu$=1746 (C=O) $cm^{-1}$.

$^1$H NMR (200 MHz, $CDCl_3$): $\delta$=0.97 (t, 3H, $CHCH_2C\underline{H}_3$, $^3J$=7.2 Hz), 1.28 (t, 3H, $OCH_2C\underline{H}_3$, $^3J$=7.2 Hz), 1.79 (m, 2H, $CHC\underline{H}_2CH_3$), 3.86 (m, 1H, $C\underline{H}CH_2CH_3$), 4.20 (m, 2H, $OC\underline{H}_2CH_3$), 4.55 (ABq, 2H, $PhC\underline{H}_2$, $^2J_{AB}$=12 Hz, $\delta_a$=4.70, $\delta_b$=4.41, $\delta_a$-$\delta_b$=0.29), 7.32 (m, 5H, aromat. H).

$^{13}$C NMR (200 MHz, $CDCl_3$): $\delta$=9.6 ($CH_3$), 14.2 ($CH_3$), 26.1 ($CH_2$), 60.6 ($CH_2$), 72.1 ($CH_2$), 79.2 (CH), 127.7 (CH), 127.9 (CH), 128.2 (CH), 137.6 (C), 172.7 (C).

MS (DCI, $NH_3$+isobutane, 90 eV), m/z (%): 240 (79) [$M^+$+$NH_4$], 223 (100) [$M^+$+H].

5-Methyl and 1-ethyl ester of (E)-2-acetoxymethyl-4-benzyloxy-4-ethylpent-2-enedioic acid (XII)

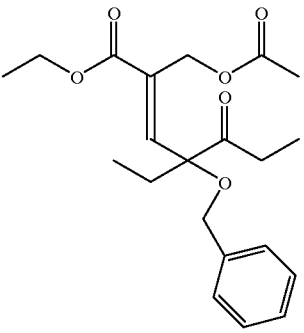

2.16 ml (4.95 mmol, 2.3M in hexane) of n-BuLi is added at –30° C. to a solution of 0.72 ml (556 mg, 5.50 mmol) of diisopropylamine in 10 ml of THF. The temperature of the mixture is allowed to rise to 0° C. and stirring is maintained for 15 minutes. The reaction medium is subsequently cooled to –80° C. and 936 mg (4.5 mmol) of methyl ester of 2-benzyloxybutyric acid, dissolved in 4 ml of THF, are added. After 15 minutes, 1.13 g (4.5 mmol) of bromide acrylate, dissolved in 6 ml of THF, are added and stirring is maintained overnight at –80° C. The temperature is allowed to rise to –40° C. and the reaction is hydrolysed with water. After extracting with $Et_2O$ and drying over $Na_2SO_4$, evaporation is carried out under reduced pressure. Purification by chromatography on silica gel (eluent: pentane/30% $Et_2O$) makes it possible to obtain 1.17 g (3.10 mmol, 69%) of oily product.

IR (Film): $\nu$=1740 (C=O), 1722 (C=O), 1657 (C=C), 1236 (Ac) $cm^{-1}$.

$^1$H NMR (200 MHz, $CDCl_3$): $\delta$=0.90 ($CCH_2C\underline{H}_3$, $^3J$=7.54 Hz), 1.27 (t, 3H, $OCH_2C\underline{H}_3$, $^3J$=7.2 Hz), 1.83 (s, 3H, (C=O)$CH_3$), 2.04 (m, 2H, $CC\underline{H}_2CH_3$), 3.76 (s, 3H, $OCH_3$), 4.22 (q, 2H, $OC\underline{H}_2CH_3$, $^3J$=7.2 Hz), 4.40 (ABq, 2H, $PhC\underline{H}_2$, $^2J_{AB}$=10.6 Hz, $\delta_a$=4.42, $\delta_b$=4.38, $\delta_a$-$\delta_b$=0.05), 5.03 (s, 2H, $C\underline{H}_2O(C=O)CH_3$), 7.28 (m, 6H, aromat. H+C=OC=C$\underline{H}$).

$^{13}$C NMR (200 MHz, $CDCl_3$): $\delta$=7.9 ($CH_3$), 14.1 ($CH_3$), 20.5 ($CH_3$), 33.1 ($CH_2$), 52.6 ($CH_3$), 58.0 ($CH_2$), 61.2 ($CH_2$), 67.2 ($CH_2$), 83.6 (C), 127.1 (CH), 127.5 (CH), 127.5 (CH), 128.0 (CH), 128.3 (CH), 131.2 (C), 137.6 (C), 143.3 (CH), 165.9 (C=O), 170.2 (C=O).

MS (high resolution, $FAB^+$): Calculated: 379.1757 ($M^+$+H) Found: 379.1783

Diethyl ester of (E)-2-acetoxymethyl-4-benzyloxy-4-ethylpent-2-enedioic acid (XII)

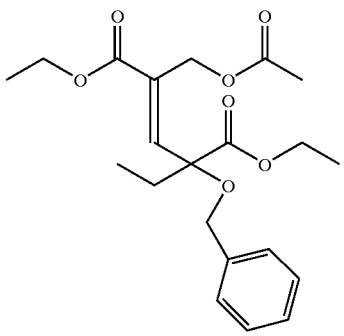

5.0 ml (11.5 mmol, 2.3M in hexane) of n-BuLi is added at –30° C. to a solution of 1.65 ml (1.27 g, 12.60 mmol) of diisopropylamine in 20 ml of THF. The temperature of the mixture is allowed to rise to 0° C. and stirring is maintained for 15 minutes. The reaction medium is subsequently cooled to −80° C. and 2.32 g (10.43 mmol) of ethyl ester of 2-benzyloxybutyric acid, dissolved in 9 ml of THF, are added. After 30 minutes, 2.62 g (10.43 mmol) of bromide acrylate, dissolved in 13 ml of THF, are added and stirring is maintained overnight at −80° C. The temperature is allowed to rise to −40° C. and the reaction is hydrolysed with water. After extracting with $Et_2O$ and drying over $Na_2SO_4$, the evaporation is carried out under reduced pressure. Purification by chromatography on silica gel (eluent: pentane/20% $Et_2O$) makes it possible to obtain 2.33 g (5.94 mmol, 57%) of oily product.

IR (Film): ν=1738 (C=O), 1656 (C=C), 1232 (Ac) $cm^{-1}$.

$^1$H NMR (200 MHz, $CDCl_3$): δ=0.91 ($CCH_2C\underline{H}_3$, $^3J$=7.2 Hz), 1.29 (m, 6H, 2×$OCH_2C\underline{H}_3$), 1.84 (s, 3H, (C=O)$C\underline{H}_3$), 2.05 (m, 2H, $CC\underline{H}_2CH_3$), 4.24 (m, 4H, 2×$OC\underline{H}_2CH_3$), 4.41 (ABq, 2H, $PhC\underline{H}_2$, $^2J_{AB}$=10.96 Hz, $δ_a$=4.43, $δ_b$=4.39, $δ_a-δ_b$=0.04), 5.04 (s, 2H, $C\underline{H}_2O$(C=O)$CH_3$), 7.29 (m, 6H, aromat. H+C=OC=C$\underline{H}$).

$^{13}$C NMR (200 MHz, $CDCl_3$): δ=8.0 ($CH_3$), 14.2 ($CH_3$), 20.6 ($CH_3$), 32.2 ($CH_2$), 58.1 ($CH_2$), 61.2 ($CH_2$), 61.8 ($CH_2$), 67.2 ($CH_2$), 83.6 (C), 127.2 (CH), 127.5 (CH), 128.3 (CH), 131.1 (C), 143.5 (CH), 166.0 (C=O), 171.4 (C=O).

MS (high resolution, $FAB^+$): Calculated: 399.1995 ($M^+$+Li) Found: 399.1995

Ethyl ester of 5-benzyloxy-5-ethyl-6-oxo-5,6-dihydro-2H-pyran-3-carboxylic acid (XIII)

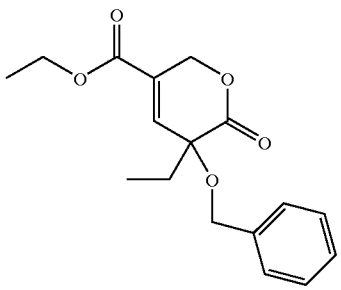

1.26 ml (1.26 mmol), 40 mol %, 1M in ethanol) of sodium ethoxide are added at room temperature to a solution of 1.19 g (3.16 mmol) of (E)-2-acetoxymethyl-4-benzyloxy-4-ethylpent-2-enedioic acid 1-ethyl ester 5-methyl ester dissolved in 30 ml of ethanol. Stirring is maintained for 3 hours and the mixture is hydrolysed with water. Extraction is carried out with $Et_2O$ and the combined ethereal phases are dried over $Na_2SO_4$ and concentrated under reduced pressure. Chromatography on silica gel (eluent: pentane/30% $Et_2O$) makes it possible to obtain 737 mg (2.42 mmol, 77%) of the expected product.

IR (Film): ν=3089, 3066, 3030, 2985, 2939, 2880, 1754 (C=O), 1721 (C=O), 1675 (C=C) $cm^{-1}$.

$^1$H NMR (200 MHz, $CDCl_3$): δ=0.96 (t, 3H, $CCH_2C\underline{H}_3$, $^3J$=7.54 Hz), 1.32 (t, 3H, $OCH_2C\underline{H}_3$, $^3J$=7.2 Hz), 1.93 (m, 2H, $CC\underline{H}_2CH_3$), 4.26 (q, 2H, $OC\underline{H}_2CH_3$, $^3J$=7.2 Hz), 4.43 (ABq, 2H, $PhC\underline{H}_2$, $^2J_{AB}$=10.6 Hz, $δ_a$=4.48, $δ_b$=4.38, $δ_a-δ_b$=0.10), 5.09 (AB of the ABX, 2H, $C\underline{H}_2C$=C),$δ_a$=5.17, $δ_b$=5.01, $δ_a-δ_b$=0.17, $^2J_{AB}$=17.3 Hz, $^4J_{AX}$=1 Hz, $^4J_{BX}$=2 Hz), 6.94 (X of the ABX, 1H, (C=O)C=CH, $^4J_{AX}$=1 Hz, $^4J_{BX}$=2 Hz), 7.31 (m, 5H, aromat. H).

$^{13}$C NMR (200 MHz, $CDCl_3$): δ=7.7 ($CH_3$), 14.0 ($CH_3$), 31.9 ($CH_2$), 61.6 ($CH_2$), 67.4 ($CH_2$), 68.5 ($CH_2$), 76.6 ($CH_2$), 127.8 (CH), 128.3 (CH), 129.5 (C), 137.4 (C), 138.8 (CH), 162.5 (C=O), 169.0 (C=O).

MS (DCI, $NH_3$+isobutane, 90 eV), m/z (%): 322 (100) $[M^++NH_4]$, 305 (29) $[M^++H]$, 214 (25) $[M^++H-CH_2C_6H_5]$.

MS ($FAB^+$, high resolution): Calculated: 305.1389 ($M^+$+H) Found: 305.1409

5-Benzyloxy-5-ethyl-6-oxo-5,6-dihydro-2H-pyran-3-carboxylic acid

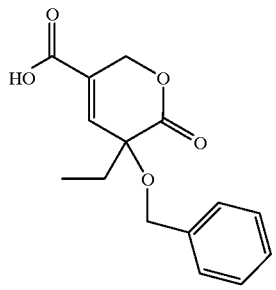

Method A

A solution of 1.45 g (4.77 mmol) of the above product of formula (XIII) and 1.26 mg (53 mmol, 11 equiv) of lithium hydroxide in 100 ml of $THF/H_2O$ (80/20) is stirred at room temperature overnight. The THF is removed under reduced pressure and the residue is extracted with diethyl ether. The aqueous phase is subsequently acidified to pH 4 with a 1N aqueous HCl solution. After extracting with $CH_2Cl_2$ (3 times), drying over $Na_2SO_4$ and evaporating under reduced pressure, 1.28 g (4.64 mmol, 97%) of product are obtained. It is pure enough to be used directly in the following reaction.

Method B

A solution of 800 mg (2.04 mmol) of the above product of formula (XIII) and 540 mg (22.4 mmol, 11 equiv) of lithium hydroxide in 64 ml of $THF/H_2O$ (80/20) is stirred at room temperature overnight. The THF is removed under reduced pressure and the aqueous phase is extracted with diethyl ether. The aqueous phase is subsequently acidified to pH4 with a 1N aqueous HCl solution. After extracting with $CH_2Cl_2$ (3 times), drying over $Na_2SO_4$ and evaporating under reduced pressure, 405 mg (1.47 mmol, 72%) of product are obtained. It is pure enough to be used directly in the following reaction.

IR (Film): ν=3437 (OH), 1728 (C=O) $cm^{-1}$.

$^1$H NMR (200 MHz $CDCl_3$): δ=0.99 (t, 3H, $CCH_2C\underline{H}_3$, $^3J$=7.54 Hz), 1.96 (m, 2H, $CC\underline{H}_2CH_3$), 4.45 (ABq, 2H, $C\underline{H}_2Ph$, $^2J_{AB}$=10.62 Hz, $δ_a$=4.51, $δ_b$=4.39, $δ_a-δ_b$=0.12), 5.10 (AB of the ABX, 2H, $C\underline{H}_2OC$=O, $^2J_{AB}$=17.48 Hz, $^4J_{AX}$=1.04 Hz, $^4J_{BX}$=2.06 Hz, $δ_a$=5.18, $δ_b$=5.02, $δ_a-δ_b$=0.16), 7.11 (X of the ABX, 1H, (C=O)C=C$\underline{H}$, $^4J_{AX}$=1.04 Hz), 7.31 (m, 5H, aromat. $_{Phenyl}$ H), 10.91 (s, 1H, $CO_2\underline{H}$).

$^{13}$C NMR (200 MHz, $CDCl_3$): δ=7.6 ($CH_3$), 31.8 ($CH_2$), 67.1 ($CH_2$), 68.7 ($CH_2$), 77.6 (C), 127.8 (CH), 127.9 (CH), 128.3 (CH), 128.7 (C), 137.1 (C), 141.6 (CH), 167.1 (C=O), 169.1 (C=O)

MS (DCI, $NH_3$+Isobutane, 90 eV), m/z (%): 294 (100) $[M^++NH_3]$, 277 (12) $[M^++H]$.

MS ($FAB^+$, high resolution): Calculated: 277.1076 ($M^+$+H) Found 277.1063

Elementary analysis:Calculated: C: 65.21 H: 5.84 Found: C: 65.26 H: 5.75

Melting point: 134° C.

2-Bromoquinolin-3-ylmethyl amide of 5-benzyloxy-5-ethyl-6-oxo-5,6-dihydro-2H-pyran-3-carboxylic acid (IV)

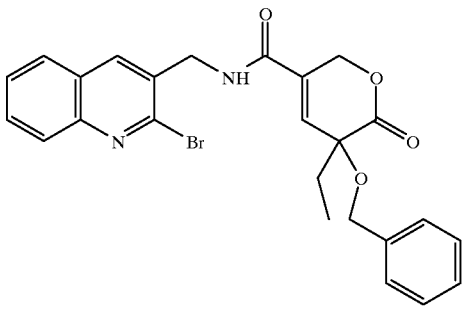

17 mg (0.14 mmol, 9%) of DMAP are added, under an argon atmosphere, to a solution of 401 mg (1.69 mmol) of the product (III) dissolved in 4 ml of $CH_2Cl_2$. The mixture is cooled to 0° C. and 351 mg (1.70 mmol) of DCC are added. 426 mg (1.54 mmol) of acid obtained in the preceding stage, dissolved in 12 ml of $CH_2Cl_2$, are subsequently added. Stirring is maintained for 3 days at room temperature. By the end of the reaction, the mixture is diluted with $Et_2O$, then filtered through celite and concentrated under reduced pressure. Purification by chromatography on silica gel (eluent: $CH_2Cl_2/20\%$ $Et_2O$) makes it possible to obtain 714 mg (1.44 mmol, 94%) of an off-white solid.

IR (Film): ν=3351 (NH), 1748 (C=O), 1685 (NHCO), 1647 (C=C) cm$^{-1}$.

$^1$H NMR (200 MHz, CDCl$_3$): δ=0.90 (t, 3H, CCH$_2$C$\underline{H}_3$, $^3J$=7.54 Hz), 1.88 (m, 2H, CC$\underline{H}_2$CH$_3$), 4.41 (ABq, 2H, PhC$\underline{H}_2$, $^2J_{AB}$=11.32 Hz, δ$_a$=4.49, δ$_b$=4.32, δ$_a$-δ$_b$=0.17), 4.60 (d, 2H, C$\underline{H}_2$N, $^3J$=5.82 Hz), 5.09 (AB of the ABX, 2H, C$\underline{H}_2$O (C=O), $^2J_{AB}$=17.12 Hz, $^2J_{AX}$=1.04 Hz, $^4J_{BX}$=2.06 Hz, δ$_a$=5.16, δ$_b$=5.02, δ$_a$-δ$_b$=0.14), 6.41 (X of the ABX, 1H, C=C$\underline{H}$), 6.77 (t, 1H, NH, $^3J$=5.48 Hz), 7.23 (m, 5H, aromat. $_{Phenyl}$ H), 7.54 (m, 1H, aromat. $_{Quino}$ H), 7.71 (m, 2H, aromat. $_{Quino}$ H), 7.95 (m, 1H, aromat. $_{Quino}$ H), 8.07 (s, 1H, aromat. $_{Quino}$ H).

$^{13}$C NMR (200 MHz, CDCl$_3$): δ=7.7 (CH$_3$), 31.9 (CH$_2$), 43.3 (CH$_2$), 67.8 (CH$_2$), 68.5 (CH$_2$), 76.4 (C), 127.1 (C), 127.6 (CH), 127.7 (CH), 127.8 (CH), 128.2 (CH), 128.4 (CH), 130.5 (C), 130.8 (CH), 132.1 (CH), 132.7 (C), 137.7 (C), 138.6 (CH), 139.1 (CH), 147.1 (C), 147.7 (C), 163.4 (C=O), 169.2 (C=O).

MS (eV), m/z (%): 497 (40) [M$^+$+H], 495 (33) [M$^+$+H] (27% of the $^{13}$C), 451 (12) [M$^+$-CO$_2$], 126 (100).

Elemental analysis: C$_{25}$H$_{23}$N$_2$O$_4$Br: Calculated: C 60.62%, H 4.68%, N 5.66% Found: C 60.43%, H 4.70%, N 5.74%

1,1,1-Triethoxy-3-trimethylsilylpropyne

TMS C(OEt)$_3$ 1,1,1-Triethoxy-3-trimethylsilylpropyne is obtained according to the protocol of Boche and coworkers [G. Boche, J. Bigalke, *Tetrahedron. Lett.*, (1984), 25, 955] from 3.84 g (20 mmol) of tetraethyl orthocarbonate in 20 ml of diethyl ether, 2.84 g (20 mmol) of borotrifluoride etherate in 20 ml of diethyl ether, 1.96 g (20 mmol) of trimethylsilylacetylene and 8.7 ml (21 mmol) of n-butyllithium (2.4M solution in hexane) in 22 ml of diethyl ether with a yield of 74% (3.17 g, 14.8 mmol). The spectroscopic data correspond to those mentioned in the reference.

3,3,3-Triethoxy-l-propyne

C(OEt)$_3$ 1.68 g of potassium carbonate are added at room temperature to a solution of 3.0 g (12.30 mmol) of 1,1,1-triethoxy-3-trimethylsilylpropyne in 180 ml of methanol. After leaving overnight, 240 ml of pentane are added and the methanol phase is separated by settling and extracted twice with pentane. The pentane phases are washed with water to pH 7. Drying over Na$_2$SO$_4$, evaporating under reduced pressure and rapid filtering through silica gel (eluent: pentane/10% Et$_2$O) makes it possible to obtain 1.4 g (8.14 mmol, 66%) of product.

The $^1$H NMR spectrum corresponds to that provided by J. C. Shattuck (see J. C. Shattuck, A. Svatoš, C. M. Blazey, J. Meinwald, Tetrahedron Lett., 38, (1997), 6803–6806).

((2-(Triethoxyprop-1-ynyl)quinolin-3-ylmethyl)amide of 5-benzyloxy-5-ethyl-6-oxo-5,6-dihydro-2H-pyran-3-carboxylic acid (V)

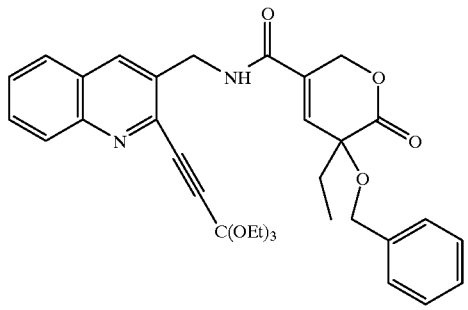

260 mg (0.52 mmol) of the product of formula (IV), 15 mg (0.079 mmol, 15 mol %) of CuI and 18 mg (0.026 mmol, 5 mol %) of PdCl$_2$(PPh$_3$)$_2$ are dissolved under an argon atmosphere in 3.3 ml of DMF and 2.2 ml of NEt$_3$. After stirring for 5 minutes, 109 mg (0.64 mmol, 1.2 equiv) of 3,3,3-triethoxy-1-propyne are added. The mixture is heated in a sealed round-bottomed flask at 80° C. for 3 hours. After hydrolyzing with water and extracting with Et$_2$O, the combined organic phases are washed 3 times with water and once with a saturated NaCl solution. Drying is carried out over NA$_2$SO$_4$ and the solvent is subsequently removed under reduced pressure. Purification on silica gel (eluent: CH$_2$Cl$_2$/20% Et$_2$O) makes it possible to obtain 240 mg (0.41 mmol, 79%) of a solid.

IR (Film): ν=3372 (NH), 2235 (C≡C), 1746 (C=O), 1683 (NHCO), 1652 (C=C), 1204-1032 (orthoester) cm$^{-1}$.

$^1$H NMR (200 MHz, CDCl$_3$): δ=0.90 (t, 3H, CCH$_2$C$\underline{H}_3$, $^3J$=7.54 Hz), 1.22 (t, 9H, 3×OCH$_2$C$\underline{H}_3$, $^3J$=7.2 Hz), 1.67 (m, 2H, CC$\underline{H}_2$CH$_3$), 3.77 (q, 6H, 3×OC$\underline{H}_2$CH$_3$, $^3J$=7.2 Hz), 4.39 (ABq, 2H, C$\underline{H}_2$Ph, $^2J_{AB}$=10.98 Hz, δ$_a$=4.41, δ$_b$=4.37, δ$_a$-δ$_b$=0.046), 4.69 (d, 2H, CH$_2$N, $^3J$=6.16 Hz), 5.09 (AB of the ABX, 2H, C$\underline{H}_{2OC=O}$, $^2J_{AB}$=17.14 Hz, $^4J_{AX}$=1.02 Hz, $^4J_{BX}$=2.06 Hz, δ$_a$=5.18, δ$_b$=5.00, δ$_a$-δ$_b$=0.18), 6.49 (X of the ABX, 1H, (C=O)C=C$\underline{H}$), 7.22 (m, 6H, 5×aromat. $_{Phenyl}$ H+NH), 7.53 (m, 1H, aromat. $_{Quino}$ H), 7.72 (m, 2H, aromat. $_{Quino}$ H), 8.04 (m, 1H, aromat. $_{Quino}$ H), 8.17 (s, 1H, aromat. $_{Quino}$ H).

$^{13}$C NMR (200 MHz, CDCl$_3$): δ=7.7 (CH$_3$), 14.9 (CH$_3$), 31.9 (CH$_2$), 42.0 (CH$_2$), 59.5 (CH$_2$), 67.8 (CH$_2$), 68.3 (CH$_2$), 88.4 (C), 109.2 (C), 127.3 (C), 127.7 (C), 127.7 (C), 128.0 (CH), 128.3 (CH), 129.0 (CH), 130.4 (CH), 132.2 (CH), 132.5 (C), 132.7 (CH), 136.7 (CH), 137.4 (C), 141.5 (C), 147.3 (C), 163.1 (C=O), 169.1 (C=O).

MS (high resolution, FAB$^+$): Calculated: 587.2757 (M$^+$+H) Found: 587.2786

Ethyl ester of [3-({[1-(5-benzyloxy-5-ethyl-6-oxo-5,6-dihydro-2H-pyran-3-yl)methanoyl]amino}-methyl)quinolin-2-yl]propionic acid

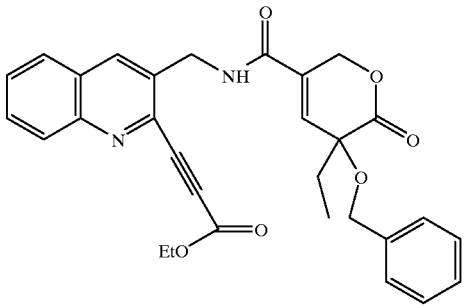

One crystal of PTSA is added to a solution of 528 mg (0.90 mmol) of product (V) obtained in the preceding stage dissolved in 17 ml of ethanol and 3.5 ml of water. Stirring is maintained at room temperature for 3 hours. The mixture is subsequently diluted with water and extracted with CH$_2$Cl$_2$. After drying the combined organic phases over Na$_2$SO$_4$, the solvent is evaporated under reduced pressure. Purification by chromatography on silica gel (eluent: CH$_2$Cl$_2$/20% Et$_2$O) makes it possible to obtain 455 mg (0.89 mmol, 99%) of product.

IR (Film): ν=3359 (NH), 1752 (C=O), 1711 (C=O), 1687 (NHCO), 1649 (C=C) cm$^{-1}$.

$^1$H NMR (200 MHz, CDCl$_3$): δ=0.91 (t, 3H, CCH$_2$C$\underline{H}_3$, $^3$J=7.54 Hz), 1.26 (t, 3H, OCH$_2$C$\underline{H}_3$, $^3$J=7.2 Hz), 1.90 (m, 2H, CC$\underline{H}_2$CH$_3$), 4.17 (q, 2H, OC$\underline{H}_2$CH$_3$, $^3$J=7.2 Hz), 4.40 (ABq, 2H, C$\underline{H}_2$Ph, $^2$J$_{AB}$=10.96 Hz, δ$_a$=4.45, δ$_b$=4.35, δ$_a$-δ$_b$=0.09), 4.72 (d, 2H, CH$_2$N, $^3$J=6.16 Hz), 5.14 (AB of the ABX, 2H, C$\underline{H}_2$OC=O, $^2$J$_{AB}$=17.3 Hz, $^4$J$_{BX}$=2.04 Hz, δ$_a$=5.22, δ$_b$=5.06, δ$_a$-δ$_b$=0.16), 6.59 (S, 1H, (C=O)C=C$\underline{H}$), 7.22 (m, 6H, 5×aromat. $_{Phenyl}$ H+NH), 7.56 (m, 1H, aromat. $_{Quino}$ H), 7.71 (m, 2H, aromat. $_{Quino}$ H), 7.98 (m, 1H, aromat. $_{Quino}$ H), 8.19 (s, 1H, aromat. $_{Quino}$ H).

$^{13}$C NMR (200 MHz CDCl$_3$): δ=7.6 (CH$_3$), 13.9 (CH$_3$), 31.9 (CH$_2$), 41.3 (CH$_2$), 62.8 (CH$_2$), 67.9 (CH$_2$), 68.3 (CH$_2$), 82.7 (C), 83.1 (C), 127.6 (CH), 127.7 (CH), 128.2 (CH), 128.8 (CH), 129.0 (CH), 130.7 (CH), 132.3 (CH), 132.8 (C), 133.1 (C), 137.0 (CH), 137.6 (CH), 139.9 (C), 147.3 (C=O), 153.3 (C=O), 163.5 (C=O).

MS (FAB, high resolution): Calculated: 513.2025 (M$^+$+H) Found: 513.2043

Elementary analysis: C$_{28}$H$_{28}$N$_2$O$_6$:

Calculated: C 70.30%, H 5.51%, N 5.47% Found: C 70.16%, H 5.65%, N 5.28%

Melting point: 68° C.

Ethyl ester of {2-[1-(5-benzyloxy-5-ethyl-6-oxo-5,6-dihydro-2H-pyran-3-yl)methanoyl]-1,2-dihydropyrrolo-[3,4-b]quinolin-3-ylidene}acetic acid (VI)

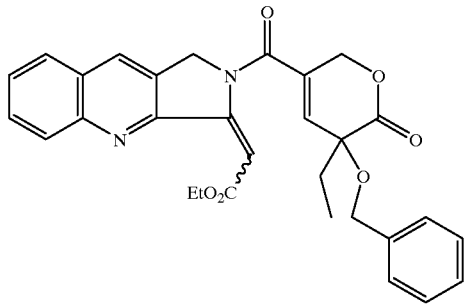

362 mg (0.353 ml, 2.33 mmol, 0.7 eq) of DBU is added, under an argon atmosphere, to a solution of 1.703 g (3.33 mmol) of product obtained in the preceding stage in 40 ml of toluene. Stirring is maintained for 30 minutes. The mixture is subsequently hydrolysed with water and excited with CH$_2$Cl$_2$. The combined organic phases are washed with water, dried over Na$_2$SO$_4$ and evaporated under reduced pressure. Purification by chromatography on silica gel (eluent: CH$_2$Cl$_2$/10% Et$_2$O) makes it possible to obtain 1.42 g (2.77 mmol, 83%) of product, the A and B isomers of which are in a 1:1 mixture. The isomers, separated by chromatography:

A

IR (Film): ν=1753 (C=O), 1699 (C=O), 1644 (C=C) cm$^{-1}$.

$^1$H NMR (200 MHz, CDCl$_3$): δ=0.94 (t, 3H, CCH$_2$C$\underline{H}_3$, $^3$J=7.54 Hz), 1.23 (t, 3H, OCH$_2$C$\underline{H}_3$, $^3$J=7.2 Hz), 1.83 (m, 2H, CC$\underline{H}_2$CH$_3$), 4.15 (q, 2H, OC$\underline{H}_2$CH$_3$, $^3$J=7.2 Hz), 4.39 (ABq, 2H, C$\underline{H}_2$Ph, $^2$J$_{AB}$=10.64 Hz, δ$_a$=4.46, δ$_b$=4.32, δ$_a$-δ$_b$=0.14), 5.10 (s, 2H, CH$_2$N), 5.31 (AB of the ABX, 2H, C$\underline{H}_2$OC=O, $^2$J$_{AB}$=16.12 Hz, $^4$J$_{BX}$=2.06 Hz, δ$_a$=5.38, δ$_b$=5.24, δ$_a$-δ$_b$=0.15), 6.19 (X of the ABX, 1H, (C=O)C=CH, $^4$J$_{BX}$=2.06 Hz), 6.59 (s, 1H, NC=CH), 7.29 (m, 5H, aromat. $_{Phenyl}$ H), 7.62 (m, 1H, aromat. $_{Quino}$ H), 7.82 (m, 2H, aromat. $_{Quino}$ H), 8.17 (m, 1H, aromat. $_{Quino}$ H), 8.21 (s, 1H, aromat. $_{Quino}$ H).

$^{13}$C NMR (300 MHz, CDCl$_3$): δ=8.2 (CH$_3$), 14.6 (CH$_3$), 31.5 (CH$_2$), 53.2 (CH$_2$), 61.0 (CH$_2$), 67.5 (CH$_2$), 68.8 (CH$_2$), 77.1 (C), 96.8 (CH), 127.8 (C), 128.0 (CH), 128.3 (CH), 128.6 (CH), 129.2 (C), 130.2 (CH), 130.8 (CH), 130.8 (CH), 131.8 (CH), 132.6 (C), 138.0 (C), 149.0 (C), 149.1 (C), 154.3 (C) 167.3 (C=O), 167.8 (C=O), 169.7 (C=O).

B

IR (Film): ν=1749 (C=O), 1714 (C=O), 1663 (C=C), 1634 (C=C) cm$^{-1}$.

$^1$H NMR (200 MHz, CDCl$_3$): δ=1.06 (t, 3H, CCH$_2$C$\underline{H}_3$, $^3$J=7.54 Hz), 1.35 (t, 3H, OCH$_2$C$\underline{H}_3$, $^3$J=7.2 Hz), 2.03 (m, 2H, CC$\underline{H}_2$CH$_3$), 4.44 (q, 2H, OC$\underline{H}_2$CH$_3$, $^3$J=7.2 Hz), 4.56 (ABq, 2H, C$\underline{H}_2$Ph, $^2$J$_{AB}$=10.98 Hz, δ$_a$=4.64, δ$_b$=4.48, δ$_a$-δ$_b$=0.159), 4.97 (ABq, 2H, C$\underline{H}_2$OC=O, $^2$J$_{AB}$=15.4 Hz, δ$_a$=5.01, δ$_b$=4.93, δ$_a$-δ$_b$=0.083), 5.14 (s, 2H, C$\underline{H}_2$N), 6.35 (s, 1H, (C=O)C=C$\underline{H}$), 7.11 (s, 1H, NC=C$\underline{H}$), 7.32 (m, 5H, aromat. $_{Phenyl}$ H), 7.54 (m, 1H, aromat. $_{Quino}$ H), 7.69 (m, 2H, aromat. $_{Quino}$ H), 7.96 (m, 1H, aromat. $_{Quino}$ H), 8.15 (s, 1H, aromat. $_{Quino}$ H).

$^{13}$C NMR (200 MHz, CDCl$_3$): δ=7.9 (CH$_3$), 14.2 (CH$_3$), 31.6 (CH$_2$), 52.6 (CH$_2$), 61.1 (CH$_2$), 67.9 (CH$_2$), 68.5 (CH$_2$), 76.6 (C), 105.7 (CH), 126.4 (C), 127.5 (CH), 127.6 (CH), 127.7 (CH), 127.8 (CH), 128.4 (CH), 129.7 (CH), 129.8 (CH), 130.0 (CH), 131.4 (CH), 133.8 (C), 137.6 (C), 148.2 (C), 152.0 (C), 165.1 (C=O), 167.4 (C=O), 169.0 (C=O).

MS (FAB+, high resolution A+B): Calculated: 513.2025 (M++H) Found: 513.2006
Ethyl ester of 4-benzyloxy-4-ethyl-3,13-dioxo-3,4,12,13,-tetrahydro-1H-2-oxa-6,12a-diazadiazadibenzo[b,h]-fluorene-5-carboxylic acid

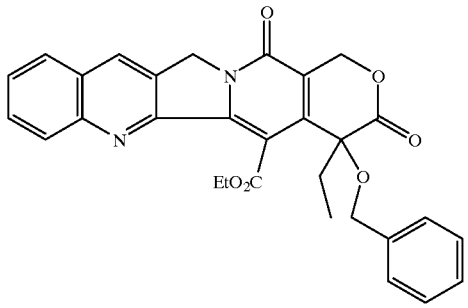

A solution of 103 mg (0.2 mmol) of the mixture of isomers of product (VI) and 26 mg (0.1 mmol) of iodine in 100 ml of $CH_2Cl_2$ is irradiated for 41 minutes in a reactor with a pyrex filter. The organic phase is washed with a saturated sodium thiosulfate solution and dried over $Na_2SO_4$. The solvent is subsequently removed under reduced pressure and the residue is purified by chromatography on silica gel (eluent: $CH_2Cl_2$/30% $Et_2O$). 30 mg (0.059 mmol, 30%) of yellowish product are obtained.

IR (Film): ν=1748 (C=O), 1725 (C=O), 1662 (C=C), 1629 (C=C) $cm^{-1}$.

$^1$H NMR (200 MHz, $CDCl_3$): δ=1.00 (t, 3H, $CCH_2C\underline{H}_3$, $^3J$=7.54 Hz), 1.22 (t, 3H, $OCH_2C\underline{H}_3$, $^3J$=7.2 Hz), 2.52 (m, 2H, $CC\underline{H}_2CH_3$), 4.51 (m, 4H, $OC\underline{H}_2CH_3$+$C\underline{H}_2Ph$), 5.27 (s, 2H, $C\underline{H}_2N$), 5.46 (ABq, 2H, C=CC$\underline{H}_2$OC=OC, $^2J_{AB}$=17.46 Hz, $δ_a$=5.65, $δ_b$=5.27, $δ_a-δ_b$=0.39), 7.23 (m, 5H, aromat. $_{Phenyl}$ H), 7.63 (m, 1H, aromat. $_{Quino}$ H), 7.76 (m, 1H, aromat. $_{Quino}$ H), 7.89 (m, 1H, aromat. $_{Quino}$ H), 8.05 (d, 1H, aromat. $_{Quino}$ H, $^3J$=7.88 Hz), 8.35 (s, 1H, aromat. $_{Quino}$ H).

$^{13}$C NMR (200 MHz, $CDCl_3$): δ=8.4 ($CH_3$), 14.5 ($CH_3$), 33.7 ($CH_2$), 50.2 ($CH_2$), 62.8 ($CH_2$), 66.7 ($CH_2$), 68.4 ($CH_2$), 79.5 (C), 108.6 (C), 122.2 (C), 126.9 (CH), 127.7 (CH), 128.1 (C), 128.3 (CH), 128.4 (CH), 128.5 (C), 128.5 (CH), 128.8 (CH), 130.2 (CH), 130.5 (CH), 130.8 (CH), 131.2 (CH), 137.9 (C), 143.9 (C), 144.3 (C), 149.0 (C), 151.7 (C=O), 156.9 (C=O), 169.0 (C=O).

MS (FAB+, high resolution): Calculated: 511.1869 (M++H) Found: 511.1862
Melting point: 92° C.
Methyl ester of [3-({[1-(5-benzyloxy-5-ethyl-6-oxo-5,6-dihydro-2H-pyren-3-yl)methanoyl]amino}methyl)quinolin-2-yl]propionic acid

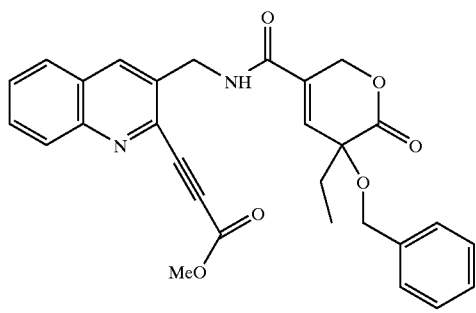

One crystal of PTSA is added, under an argon atmosphere, to a solution of 686 mg (1.20 mmol) of product (V) in 34 ml of methanol. Stirring is maintained for 2 hours at room temperature and the reaction medium is subsequently diluted with water. After 30 minutes, the suspension is extracted with $CH_2Cl_2$ and the organic phases are dried over $Na_2SO_4$ and evaporated under reduced pressure. Purification on silica gel (eluent: $CH_2Cl_2$/10% $Et_2O$) makes it possible to isolate 380 mg (0.76 mmol, 63%) of the expected product and 115 mg (0.23 mmol, 19%) of ethyl ester.

IR (Film): ν=3356 (NH), 1756 (C=O), 1718 (C=O), 1693 (NHCO), 1659 (C=C) $cm^{-1}$.

$^1$H NMR (300 MHz, $CDCl_3$): δ=0.87 (t, 3H, $CCH_2C\underline{H}_3$, $^3J$=7.41 Hz), 1.85 (m, 2H, $CC\underline{H}_2CH_3$), 3.67 (s, 3H, $OCH_3$), 4.36 (ABq, 2H, $C\underline{H}_2Ph$, $^2J_{AB}$=10.98 Hz, $δ_a$=4.41, $δ_b$=4.30, $δ_a-δ_b$=0.11), 4.66 (d, 2H, $CH_2N$, $^3J$=6.03 Hz), 5.09 (AB of the ABX, 2H, $C\underline{H}_2OC$=O, $^2J_{AB}$=17.28 Hz, $^4J_{AX}$=0.78 Hz, $^4J_{BX}$=2.16 Hz, $δ_a$=5.20, $δ_b$=5.04, $δ_a-δ_b$=0.16), 6.51 (X of the ABX, 1H, (C=O)C=CH, $^4J$=1.41 Hz), 7.15 (m, 6H, 5×aromat. $_{Phenyl}$ H+NH), 7.52 (m, 1H, aromat. $_{Quino}$ H), 7.67 (m, 2H, aromat. $_{Quino}$ H), 7.94 (m, 1H, aromat. $_{Quino}$ H), 8.14 (s, 1H, aromat. $_{Quino}$ H).

$^{13}$C NMR (300 MHz, $CDCl_3$): δ=8.1 ($CH_3$), 32.4 ($CH_2$), 41.7 ($CH_2$), 53.6 ($CH_3$), 68.3 ($CH_2$), 68.8 ($CH_2$), 76.8 (C), 83.2 (C), 83.5 (C), 128.1 (CH), 128.1 (CH), 128.2 (C), 128.7 (CH), 129.3 (CH), 129.5 (CH), 131.2 (CH), 132.8 (CH), 133.3 (C), 133.5 (C), 137.5 (C), 137.5 (CH), 138.1 (C), 140.2 (C), 147.8 (C), 154.1 (C=O), 164.0 (C=O), 167.6 (C=O).

MS (DCI, $NH_3$+isobutane, 90 eV), m/z (%): 499 (100) [M++H], 392 (9) [M+—$OCH_2Ph$].
Melting point: 75° C.
Methyl ester of {2-[1-(5-benzyloxy-5-ethyl-6-oxo-5,6-dihydro-2H-pyren-3-yl)methanoyl]-1,2-dihydropyrrolo-[3,4-b]quinolin-3-ylidene}acetic acid

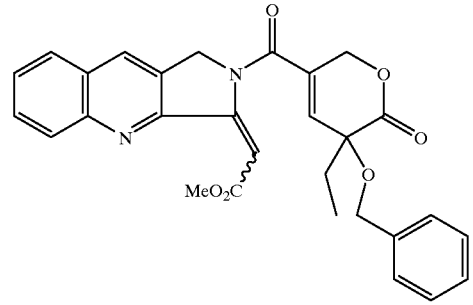

0.48 ml (0.53 mmol, 0.7 eq) of DBU is added, under an argon atmosphere, to a solution of 380 mg (0.76 mmol) of the compound obtained in the preceding stage in 8.2 ml of toluene. Stirring is maintained for 30 minutes. The mixture is subsequently hydrolysed with water and extracted with $CH_2Cl_2$. The combined organic phases are washed with water, dried over $Na_2SO_4$ and evaporated under reduced pressure. Purification by chromatography on silica gel (eluent: $CH_2Cl_2$/20% $Et_2O$) makes it possible to obtain 240 mg (0.48 mmol, 63%) of product in the form of two isomers A and B in a 1:1 ratio. The isomers, separated by chromatography:

A

IR (Film): ν=1755 (C=O), 1696 (C=ON), 1649 (C=C) $cm^{-1}$.

$^1$H NMR (200 MHz, $CDCl_3$): δ=0.94 (t, 3H, $CCH_2C\underline{H}_3$, $^3J$=7.54 Hz), 1.83 (m, 2H, $CC\underline{H}_2CH_3$), 3.69 (s, 3H, $OC\underline{H}_3$), 4.39 (ABq, 2H, $C\underline{H}_2Ph$, $^2J_{AB}$=10.64 Hz, $δ_a$=4.45, $δ_b$=4.32, $δ_a-δ_b$=0.13), 5.07 (s, 2H, $CH_2N$), 5.31 (AB of the ABX, 2H, $CH_2OC$=O,$^2J_{AB}$=16.1 Hz, $^4J_{AX}$=1.72 Hz, $^4J_{BX}$=1.36 Hz, $\delta_a$=5.37, $\delta_b$=5.23, $\delta_a$-$\delta_b$=0.14), 6.21 (X of the ABX, 1H, OCH$_2$C=C$\underline{H}$), 6.58 (s, 1H, C=CH), 7.25 (m, 5H, aromat. $_{Ph}$ H), 7.61 (m, 1H, aromat. $_{Quino}$ H), 7.81 (m, 2H, aromat. $_{Quino}$ H), 8.16 (m, 2H, aromat. $_{Quino}$ H).

MS (DCI, NH$_3$+isobutane, 90 eV) m/z (%): 516 (5) [M$^+$+NH$_4$], 499 (100) [M$^+$+H], 407 (5), 392 (28), 241 (14).

B

IR (Film): $\nu$=1754 (C=O), 1717 (C=ON), 1665 (C=C) cm$^{-1}$.

$^1$H NMR (200 MHz, CDCl$_3$): $\delta$=1.06 (t, 3H, CCH$_2$C$\underline{H}_3$, $^3$J=7.54 Hz), 1.92 (m, 2H, CC$\underline{H}_2$CH$_3$), 3.92 (s, 3H, OC$\underline{H}_3$), 4.55 (ABq, 2H, C$\underline{H}_2$Ph, $^2$J$_{AB}$=11.3 Hz, $\delta_a$=4.63, $\delta_b$=4.48, $\delta_a$-$\delta_b$=0.145), 4.96 (AB of the ABX, 2H, CH$_2$OC=O, $^2$J$_{AB}$=16.1 Hz, $^4$J$_{AX}$=1.72 Hz, $\delta_a$=5.00, $\delta_b$=4.92, $\delta_a$-$\delta_b$= 0.079), 5.13 (s, 2H, CH$_2$N), 6.36 (s, 1H, C=CH), 7.11 (s, 1H, C=CH), 7.31 (m, 5H, aromat. $_{Ph}$ H), 7.49 (m, 1H, aromat. $_{Quino}$ H), 7.66 (m, 2H, aromat. $_{Quino}$ H), 7.93 (m, 2H, aromat. $_{Quino}$ H).

MS (DCI, NH$_3$+isobutane, 90 eV) m/z (%): 499 (76) [M$^+$+H], 392 (12) [M$^+$-[lacuna]], 241 (100).

Camptothecin

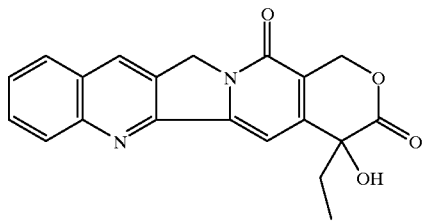

A solution of 20 mg (0.04 mmol) of the photochemical product obtained above in 1 ml of HBr (48% aqueous solution) is heated in a sealed tube at 40° C. for 3.5 hours. The reaction solution is neutralized with a saturated NaHCO$_3$ solution. The aqueous phase is subsequently extracted 5 times with CH$_2$Cl$_2$ and the combined organic phases are dried over Na$_2$SO$_4$ and evaporated under reduced pressure.

Analysis by HPLC ($\mu$ Bondapak C-18, 3.9×300 mm, H$_2$O:acetonitrile:formic acid (50:50:0.5), Rt=3.95 min) of the reaction mixture after filtering through silica gel showed an approximate yield of camptothecin of 3%. The identity of the camptothecin, purified by chromatography on silica and by HPLC (several combined experiments), was confirmed by comparison of the mass spectrum and of the $^1$H NMR spectrum with those of commercial camptothecin.

What is claimed is:

1. Process for the preparation of camptothecin, or of at least one derivative of formula (I):

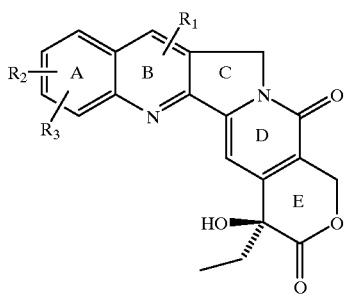

(I)

wherein R$_1$, R$_2$, and R$_3$ each represent an identical or different group chosen from:
- hydrogen,
- a hydroxyl group,
- a halogen atom, chosen from fluorine, chlorine, bromine, or iodine,
- a linear or branched alkoxy group comprising 1 to 4 carbon atoms,
- a linear or branched alkylthio group comprising 1 to 4 carbon atoms,
- a (C$_1$-C$_4$)alkylamino group, optionally substituted by one or more C$_1$-C$_4$ alkyl groups,
- an aralkyl group, optionally substituted by a C$_1$-C$_4$ alkyl group, wherein said aryl group is optionally a heterocycle with 1 to 3 heteroatoms chosen from oxygen, sulfur, and nitrogen, and
- an arylcarbonyloxy group, wherein said aryl group is optionally a mono- or polycyclic heterocycle with 1 to 3 heteroatoms chosen from oxygen, sulfur, and nitrogen;

comprising condensing a 3-(aminomethyl)quinoline derivative and a 5-hydroxy-5-ethyl-6-oxo-5,6-dihydropyrancarboxylic acid or acid derivative, followed by an ethynylation stage, and optionally by at least one of a hydrolysis stage, a double cyclization stage, a dehydrogenation, and a deprotection/dealkoxycarbonylation.

2. Process according to claim 1, wherein the compound of formula (I) is at least one compound chosen from:
- camptothecin, wherein R$_1$, R$_2$, and R$_3$ are hydrogen,
- topotecan or Hycamtin®, wherein R$_1$ is hydrogen, R$_2$ is a dimethylaminomethyl group, and R$_3$ is a hydroxyl group,
- irinotecan or Campto®, wherein R$_1$ is an ethyl group, R$_2$ is a piperidinopiperidinocarbonyloxy group, and R$_3$ is hydrogen.

3. Process according to claim 1, wherein said 5-hydroxy-5-ethyl-6-oxo-5,6-dihydropyrancarboxylic acid or acid derivative is of formula:

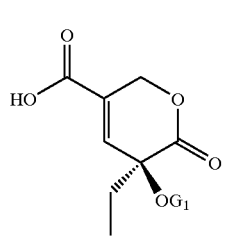

(II)

wherein G$_1$ is hydrogen or a protective group for a hydroxyl group, and wherein said 3-(aminomethyl)quinoline derivative is of general formula:

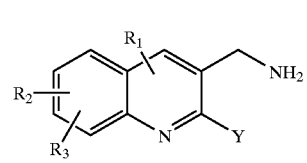

(III)

wherein R$_1$, R$_2$, and R$_3$ are as defined in formula (I) in claim 1, or are protected radicals or radicals which optionally easily converted to R$_1$, R$_2$, and R$_3$ radicals defined previously, and Y is a leaving group, further comprising obtaining a quinoline derivative of formula:

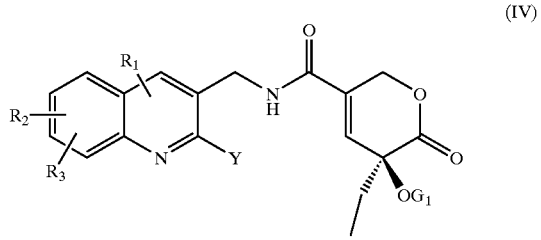

(IV)

wherein $G_1$, $R_1$, $R_2$, $R_3$, and Y are defined as above.

4. Process according to claim 3, wherein $G_1$ is chosen from a hydrogen, benzyl, para-methoxybenzyl, methoxymethyl, tert-butyl, and trialkylsilyl group, wherein at least one alkyl group in the trialkylsilyl group has more than two carbon atoms.

5. Process according to claim 4, wherein $G_1$ is a benzyl group.

6. Process according to claim 4, wherein Y is chosen from a halogen atom or an $OSO_2R$ group wherein R is an alkyl, tolyl, naphthyl, or trifluoromethyl group.

7. Process according to claim 6, wherein Y is chosen from bromine, iodine, and trifluoromethylsulfonate.

8. Process according to claim 3, wherein the acid or acid derivative of formula (II) is chosen from at least one of an acid chloride, an anhydride, a mixed anhydride, a reactive ester, or an ammonium or pyridinium acyl intermediate.

9. Process according to claim 3, wherein a reaction temperature is between $-40$ and $+40°$ C.

10. Process according to claim 3, wherein a solvent is chosen from at least one organic solvent.

11. Process according to claim 3, wherein a reaction is carried out in the presence of an acid acceptor.

12. Process according to claim 11, wherein the acid acceptor is a nitrogenous organic base and is chosen from at least one of pyridine, dimethylaminopyridine, N-methylmorpholine, and trialkylamine.

13. Process according to claim 3, wherein a reaction is carried out in the presence of a coupling agent chosen from at least one of carbodiimide, N,N'-carbonyldiimidazole, and 2-ethoxy-1-ethoxycarbonyl-1,2-dihydroquinoline.

14. Process according to claim 1, wherein the ethynylation is carried out by reaction in the presence of a trialkyl (optionally substituted $C_1$–$C_4$) orthopropiolate or of an alkyl (optionally substituted $C_1$–$C_4$) propiolate, and of a palladium complex, copper iodide, and a base, to give the quinoline derivative of formula:

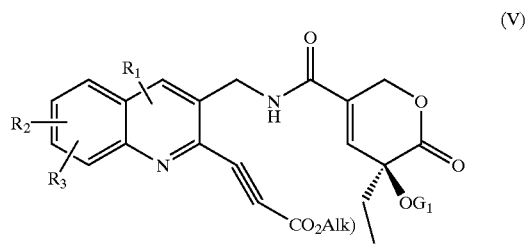

(V)

wherein $R_1$, $R_2$, $R_3$, and $G_1$ are defined as above, and Alk is a $C_1$–$C_4$ alkyl group, optionally substituted by an aryl or heteroaryl group.

15. Process according to claim 14, wherein the palladium complex is chosen from at least one of tris (dibenzylideneacetone)dipalladium, bis(benzonitrile) palladium chloride, or dichlorobis(triphenylphosphine) palladium.

16. Process according to claim 14, wherein the base is chosen from at least one of a tertiary amine or an alkaline carbonate.

17. Process according to claim 14, further comprising a subsequent hydrolysis stage wherein the reaction is carried out in the presence of trialkyl (optionally substituted $C_1$–$C_4$) orthopropiolate.

18. Process according to claim 14, wherein the condensation is carried out in an inert organic solvent.

19. Process according to claim 14, wherein the condensation is carried out at a temperature of between 20 and 110° C.

20. Process according to claim 14, further comprising cyclizing the derivative of formula (V) by addition of a base to give a tetracyclic derivative of general formula (VI):

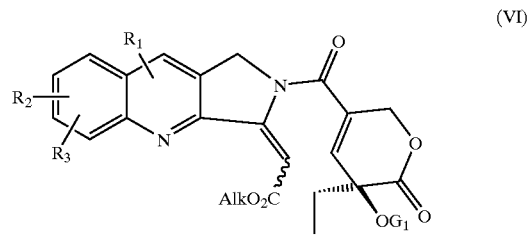

(VI)

wherein Alk, $R_1$, $R_2$, $R_3$ and $G_1$ are as defined.

21. Process according to claim 20, wherein the base is chosen from at least one of DBU (1,8-diazabicycloundec-7-ene), DBN (1,5-diazabicyclonon-5-ene, and DABCO (1,4-diazabicyclooctane.

22. Process according to claim 20, wherein the cyclization is carried out in an anhydrous medium, in an inert organic solvent, at a temperature of between $-30$ and $+30°$ C.

23. Process according to claim 1, further comprising cyclizing the compound of formula (VI) in order to give at least one ester of camptothecin and of its derivative of formula:

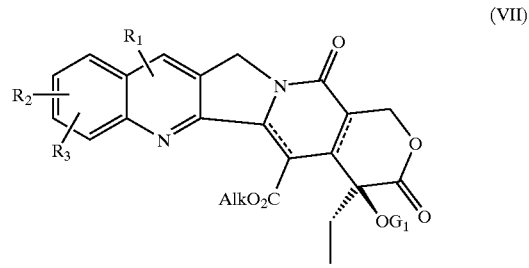

(VII)

wherein $R_1$, $R_2$, $R_3$, Alk, and $G_1$ are as defined above, and dotted lines are optional double bonds.

24. Process according to claim 23, wherein the cyclization is carried out by irradiation.

25. Process according to claim 24, wherein the irradiation is carried out alone, or in the presence of an oxidizing agent.

26. Process according to claim 25, wherein the oxidizing agent is iodine.

27. Process according to claim 25, or 26, wherein the irradiation is carried out in an halogenated aliphatic solvent.

28. Process according to claim 24, wherein the irradiation is carried out at a temperature of between $-30°$ C. and 50° C.

29. Process according to claim 23, wherein the derivative of formula (VII) lacks the optional double bonds and Alk is a methyl group substituted by an aryl or heteroaryl group, further comprising hydrogenating in the presence of a palladium catalyst to give the acid, converting said acid to at least one of camptothecin and its derivatives by the action of palladium and cymene at high temperature, optionally followed by deprotecting the hydroxyl group in the lactone.

30. Process according to claim 23, wherein the derivative of formula (VII) above, which has one optional double bond or neither optional double bond, can be treated with DDQ (dichlorodicyanobenzoquinone) to give the compound of formula (VII) with both optional double bonds.

31. Process according to claim 1, wherein the derivative of formula (VII) has two double bonds in the lactone and in the piperidine ring further comprising deprotecting and dealkoxycarbonylating by the action of hydrobromic acid to give to at least one of camptothecin or its derivatives of formula (I)

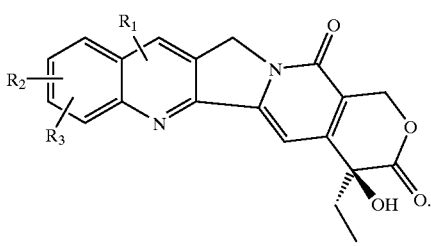

(I)

32. Process according to claim 31, wherein deprotecting and dealkoxycarbonylating are carried out at a temperature of between 50 and 140° C.

33. A compound of formula:

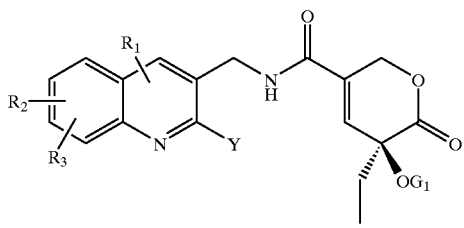

(IV)

wherein $R_1$, $R_2$, $R_3$ each represent an identical or different group chosen from:
hydrogen,
a hydroxyl group,
a halogen atom, chosen from fluorine, chlorine, bromine, or iodine,
a linear or branched alkoxy group comprising 1 to 4 carbon atoms,
a linear or branched alkylthio group comprising 1 to 4 carbon atoms,
a ($C_1$–$C_4$)alkylamino group, optionally substituted by one or more $C_1$–$C_4$ alkyl groups,
an aralkyl group, optionally substituted by a $C_1$–$C_4$ alkyl group, wherein said aryl group are optionally a heterocycle with 1 to 3 heteroatoms chosen from oxygen, sulfur, and nitrogen, and
an arylcarbonyloxy group, wherein said aryl group is optionally a mono- or polycyclic heterocycle with 1 to 3 heteroatoms chosen from oxygen, sulfur, and nitrogen;

wherein Y is a leaving group, and $G_1$ is hydrogen or a protective group for an hydroxyl functional group.

34. A compound according to claim 33, wherein Y is chosen from a halogen atom or an $OSO_2R$ group where R represents an alkyl, tolyl, naphthyl, trifluoromethyl group.

35. A compound of formula (V)

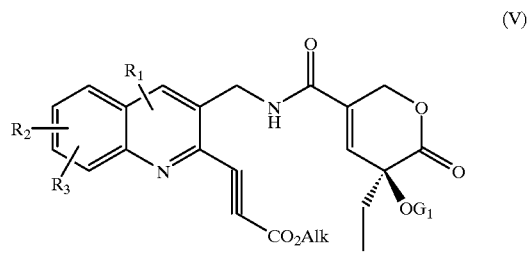

(V)

wherein $R_1$, $R_2$, and $R_3$ each represent an identical or different group chosen from:
hydrogen,
a hydroxyl group,
a halogen atom chosen from fluorine, chlorine, bromine, or iodine,
a linear or branched alkoxy group comprising 1 to 4 carbon atoms,
a linear or branched alkylthio group comprising 1 to 4 carbon atoms,
a ($C_1$–$C_4$)alkylamino group, optionally substituted by one or more $C_1$–$C_4$ alkyl groups,
an aralkyl group, optionally substituted by a $C_1$–$C_4$ alkyl group, wherein said aryl group is optionally a heterocycle with 1 to 3 heteroatoms chosen from oxygen, sulfur, and nitrogen,
an arylcarbonyloxy group, wherein said aryl group is optionally a mono- or polycyclic heteroatoms with 1 to 3 heteroatoms chosen from oxygen, sulfur, and nitrogen,
$G_1$ is hydrogen or a protective group for a hydroxyl group, and Alk is a $C_1$–$C_4$ alkyl group optionally substituted by at least one aryl or heteroaryl group.

36. A compound of formula

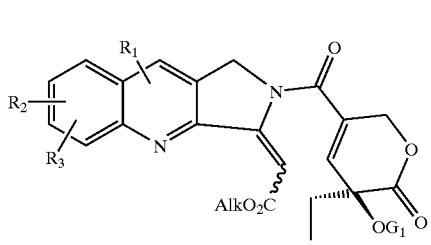

(VI)

wherein $R_1$, $R_2$, and $R_3$ each represent an identical or different group chosen from:
hydrogen,
a hydroxyl group,
a halogen atom chosen from fluorine, chlorine, bromine or iodine,
a linear or branched alkoxy group comprising 1 to 4 carbon atoms,
a linear or branched alkylthio group comprising 1 to 4 carbon atoms,
a ($C_1$–$C_4$)alkylamino group, optionally substituted by one or more $C_1$–$C_4$ alkyl groups, an aralkyl group, optionally substituted by a $C_1$–$C_4$ alkyl group, wherein said aryl group is optionally a heterocycle with 1 to3 heteroatoms chosen from oxygen, sulfur, and nitrogen, and an arylcarbonyloxy group, wherein said aryl group is optionally a mono- or polycyclic heterocycle with 1 to 3 heteroatoms chosen from oxygen, sulfur, and nitrogen;

$G_1$ is hydrogen or a protective group for an alcohol functional group; and Alk is a $C_1$–$C_4$ alkyl group optionally substituted by at least one aryl or heteroaryl group.

37. Process according to claim 19, wherein the temperature is between 20 and 80° C.

38. Process according to claim 10, wherein the at least one organic solvent is a chlorinated solvent.

39. Process according to claim 11, wherein the acid acceptor is a nitrogenous organic base.

40. Process according to claim 18, wherein the inert organic solvent is chosen from ether and amide.

41. Process according to claim 40, wherein the amide is chosen from acetamide and dimethylformamide.

42. Process according to claim 22, wherein the inert organic solvent is an aromatic solvent.

43. Process according to claim 24, wherein the irradiation is carried out, in the presence of a reducing agent.

44. Process according to claim 43, wherein the reducing agent is borohydride.

45. Process according to claim 43 or 44, wherein the irradiation is carried out in at least one alcohol.

* * * * *

UNITED STATES PATENT AND TRADEMARK OFFICE
CERTIFICATE OF CORRECTION

PATENT NO. : 6,486,320 B2
DATED : November 26, 2002
INVENTOR(S) : Stefanie Leue et al.

It is certified that error appears in the above-identified patent and that said Letters Patent is hereby corrected as shown below:

<u>Column 22,</u>
Line 55, after "of", delete "general".
Line 66, after "which", insert -- are --.

<u>Column 23,</u>
Lines 52-60, in formula (V), "$CO_2Alk)$" should read -- $CO_2Alk$ --.

<u>Column 24,</u>
Line 2, "or" should read -- and --.
Line 29, "$G_1$are as defined." should read -- $G_1$ are as defined above. --.
Lines 31-33, "(1,8-diazabicycloundec-7-ene), DBN (1,5-diazabicyclonon-5-ene, and DABCO (1,4-diazabicyclooctane." should read -- (1,8-diazabicyclo[5.4.0]undec-7-ene), DBN (1,5-diazabicyclo[5.4.0]non-5-ene, and DABCO (1,4-diazabicyclo[2.2.2]octane. --.

<u>Column 24,</u>
Line 58, "alone, or" should read -- alone or --.

<u>Column 25,</u>
Line 16, after "give", delete "to".
Line 16, "derivatives" should read -- derivative --.
Line 61, "group are"should read -- group is --.

<u>Column 26,</u>
Line 37, "polycyclic heteroatoms" should read -- polycyclic heterocycle --.

<u>Column 27,</u>
Line 3, "1 to3" should read -- 1 to 3 --.
Line 10, "$C_1$ -$C_4$" should read --$C_1$-$C_4$--.

UNITED STATES PATENT AND TRADEMARK OFFICE
CERTIFICATE OF CORRECTION

PATENT NO.    : 6,486,320 B2
DATED         : November 26, 2002
INVENTOR(S)   : Stefanie Leue et al.

It is certified that error appears in the above-identified patent and that said Letters Patent is hereby corrected as shown below:

Column 28,
Line 10, "out, in" should read -- out in --.

Signed and Sealed this

Fourth Day of May, 2004

JON W. DUDAS
*Acting Director of the United States Patent and Trademark Office*